United States Patent
Yoshida et al.

(10) Patent No.: US 9,671,505 B2
(45) Date of Patent: Jun. 6, 2017

(54) RADIATION MEASURING DEVICE (71) Applicant: HITACHI ALOKA MEDICAL, LTD., Mitaka-shi, Tokyo (JP)

(72) Inventors: Norio Yoshida, Mitaka (JP); Toshikazu Tanino, Mitaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/903,736

(22) PCT Filed: Aug. 20, 2014

(86) PCT No.: PCT/JP2014/071734
§ 371 (c)(1),
(2) Date: Jan. 8, 2016

(87) PCT Pub. No.: WO2015/025870
PCT Pub. Date: Feb. 26, 2015

(65) Prior Publication Data
US 2016/0170036 A1     Jun. 16, 2016

(30) Foreign Application Priority Data

Aug. 22, 2013 (JP) ................. 2013-172454

(51) Int. Cl.
*G02B 1/00* (2006.01)
*G01T 1/169* (2006.01)

(52) U.S. Cl.
CPC ...... *G01T 1/169* (2013.01); *G01N 2201/0221* (2013.01)

(58) Field of Classification Search
CPC ............ G01J 1/0233; G01J 2001/0257; G01N 2201/0221; B23K 26/0096
(Continued)

(56) References Cited

U.S. PATENT DOCUMENTS

| 4,634,294 A | * 1/1987 | Christol ............ G01J 5/02 340/584 |
| 4,889,991 A | 12/1989 | Ramsey et al. |

(Continued)

FOREIGN PATENT DOCUMENTS

| JP | 2-198385 A | 8/1990 |
| JP | 2001-4757 A | 1/2001 |

(Continued)

OTHER PUBLICATIONS

Notification of Transmittal of Translation of the International Preliminary Report on Patentability (Form PCT/IB/326) of International Application No. PCT/JP2014/071734 mailed Mar. 3, 2016 with Forms PCT/IB/373, PCT/ISA/237, PCT/IB/338 and PCT/IB/308 (Second and Supplementary Notice). (14 pages).

(Continued)

*Primary Examiner* — David J Makiya
*Assistant Examiner* — Kenneth J Malkowski
(74) *Attorney, Agent, or Firm* — Westerman, Hattori, Daniels & Adrian, LLP (57) ABSTRACT

In the present invention, a battery box is provided on the lower side of a survey meter body so as to protrude downwardly. Four primary batteries are accommodated inside the battery box with inclined postures. A stepped structure is formed between the front surface of the battery box and the lower surface of the body. The survey meter can be held by a hand while an index finger, or the like, is hooked on the stepped structure. It is also possible to remove the battery box and dispose a plate-like secondary battery in an accommodation space.

5 Claims, 7 Drawing Sheets

(58) Field of Classification Search
USPC .................................................... 250/504 H
See application file for complete search history.

(56) References Cited

U.S. PATENT DOCUMENTS

| | | | | |
|---|---|---|---|---|
| 5,820,462 | A * | 10/1998 | Yokoi | A63F 13/06 273/148 B |
| 5,973,757 | A * | 10/1999 | Aubuchon | H03J 1/0025 340/12.55 |
| 2005/0230628 | A1 | 10/2005 | Hirai et al. | |
| 2007/0066394 | A1 * | 3/2007 | Ikeda | A63F 13/06 463/37 |
| 2008/0179522 | A1 * | 7/2008 | Vallon | G01T 1/167 250/336.1 |
| 2015/0192680 | A1 | 7/2015 | Obata et al. | |

FOREIGN PATENT DOCUMENTS

| | | |
|---|---|---|
| JP | 2004-93456 A | 3/2004 |
| JP | 5042383 B1 | 10/2012 |
| JP | 2013-53881 A | 3/2013 |
| NO | 2007/109535 A2 | 9/2007 |
| WO | 2004/019060 A1 | 3/2004 |

OTHER PUBLICATIONS

International Search Report dated Oct. 14, 2014, issued in counterpart International Application No. PCT/JP2014/071734 (2 pages).
"Operation Manual for the Monitor 4, Monitor 4EC, and MC1K", S.E. International Inc., Feb. 1, 2001, (10 pages). Cited in extended (Supplementary) European Search Report dated Mar. 21, 2017.
Extended (Supplementary) Search Report dated Mar. 21, 2017, issued in counterpart European Application No. 14837678.3 (9 pages).

* cited by examiner

RADIATION MEASURING DEVICE

TECHNICAL FIELD

The present invention relates to a radiation measurement device, and particularly to a form of a portable radiation measurement device.

BACKGROUND ART

Survey meters are known as portable radiation measurement devices. Survey meters are devices for measuring, for example, environmental radiation and radiation from radioactive pollution sources. Patent Document 1 discloses a survey meter having a flat-plate shape as a whole. The survey meter has a tip portion, a middle portion, and a grip portion. The tip portion is connected to the middle portion via a bending portion. A display and an operating portion are provided on the upper surface of the middle portion. The grip portion has a thin flat form when seen from the horizontal direction and houses therein plate-shaped batteries as rechargeable secondary batteries.

CITATION LIST

Patent Document

[Patent Document 1] JP 5042383 B

SUMMARY OF INVENTION

Technical Problem

As a power source for a portable survey meter, not only secondary batteries but also primary batteries are used. If the latter, primary batteries, are used, in order to ensure sufficient capacity, there is a need to provide a structure in which a plurality of (for example, four) primary batteries can be set. In the case of the flat-plate shaped survey meter, it does not have sufficient space for housing a plurality of primary batteries in its body. Although it is possible to provide a battery box so as to protrude from the body, the retention and the operability are deteriorated if the battery box is positioned carelessly. For example, if the battery box is additionally connected side-by-side to the grip portion along the horizontal direction, although the original shape of the grip portion can be maintained, the weight balance is lost to a great extent, and the operability is deteriorated. If the battery box is provided on the upper side of the grip portion, the operability is also deteriorated.

The object of the present invention is to enhance the operability of the hand-held radiation measurement device having an enlarged battery box. Alternatively, the object of the present invention is to realize, in the radiation measurement device having the battery box, a grip form that can be held in the hand smoothly.

Solution to Problem

A portable radiation measurement device according to the present invention has a body that has a tip portion for detecting radiation and a grip portion, a battery box that has a form protruding downward on the lower side of the grip portion and houses one or more batteries, and in this device, a lower surface of the body and a front surface of the battery box form a stepped structure on the lower side of the body.

With the above-described structure, the battery box is provided on the lower side of the grip portion of the body, and one or more batteries in the battery box supply electrical power to electronic devices in the body. Preferably, the battery box houses a plurality of primary batteries (cylindrical batteries) in an exchangeable manner. The battery box is preferably structured so as to be removable when the plurality of primary batteries are not used. In that case, preferably, for example, a thin flat-plate shaped secondary battery is housed in the battery space in the body. In the above-described structure, the front surface of the battery box and the lower surface of the body form a stepped structure.

Preferably, the battery box and the grip portion as a whole are held in the hand by placing, for example, the index finger on the stepped structure. It is also possible to place two fingers on the stepped structure. Such placement of the finger naturally prevents the radiation measurement device from slipping off forward from the hand. For example, upon measurement of air dose or upon measurement of radiation from an object, the body is often positioned in a horizontal posture or in a slightly forward inclined posture. By placing the finger on the stepped structure while the body is in such a posture, it is possible to hold the radiation measurement device easily in a stable manner without using force. Preferably, the grip portion has a flat-plate shape; that is, a generally flat form. By forming the grip portion to have a neck shape when seen from above, it can be held in the hand more easily. Because, while the finger is placed on the stepped structure, the posture of the radiation measurement device is stabilized as described above, and, for example, even if the operating portion on the upper surface of the body is operated by the thumb, the posture of the radiation measurement device is not seriously unbalanced, or the radiation measurement device does not slip off forward from the hand. When the battery box is removed, and the grip portion is held in the hand, a hook corresponding to the above-described stepped structure may be provided separately to support such holding. There is no need for placing the finger always on the stepped structure, and it is performed as necessary.

Preferably, the one or more batteries are housed in the battery box so as to be in a posture inclined to the body. If there is a battery housing space in the body, one or more batteries may be arranged such that part of the one or more batteries are inserted into the battery housing space. In doing so, it is possible to reduce the amount of downward protrusion of the battery box. If the one or more batteries are arranged in an inclined posture, the lower surface of the battery box for housing them naturally becomes an inclined surface. In that case, the amount of downward protrusion of the battery box gradually increases from the front end to the rear end. Such a form of the battery box fits the hand when it is held in the hand.

Preferably, an angle between the lower surface of the body and the front surface of the battery box is less than 90 degrees. With this structure, the finger is easily placed on the stepped structure. For example, when measurement is carried out by placing the body in a forward inclined posture, compared to the case of an angle of 90 degrees, a better finger placement state is achieved with an angle of less than 90 degrees.

Preferably, the lower surface of the battery box is inclined to the lower surface of the body. As described above, if the amount of downward protrusion of the battery box gradually increases from the front end to the rear end thereof, the battery box can be held in the hand smoothly.

Preferably, the body has the tip portion, a middle portion provided on the rear side of the tip portion, and the grip portion provided on the rear side of the middle portion, and the body extends in the longitudinal direction, the center of gravity of the radiation measurement device being near the step in the longitudinal direction.

With the above-described structure, the center of gravity is positioned near the finger placed on the stepped structure. Therefore, if the body is in a horizontal posture, it is possible to maintain such a posture in a stable manner without holding the battery box or the grip portion firmly in the hand. Thus, the load of operation can be alleviated. If the tip portion is bent diagonally downward with respect to the middle portion, hang-down forms are formed on both sides of the stepped structure, and the center of gravity is lowered downward. In that case, when the finger is placed on the stepped structure, the radiation measurement device is positioned on that finger like a balancing toy. In such a state, even if the radiation measurement device is inclined to one side or inclined to another side, the posture restoring force acts. If the radiation measurement device is held in such a state, the load for stabilizing the posture of the radiation measurement device is alleviated largely. The position of the center of gravity is preferably set within the range where the stabilized posture as described above can be obtained.

DESCRIPTION OF EMBODIMENT

Hereinafter, a preferred embodiment of the present invention will be described by reference to the drawings.

Figure 1:
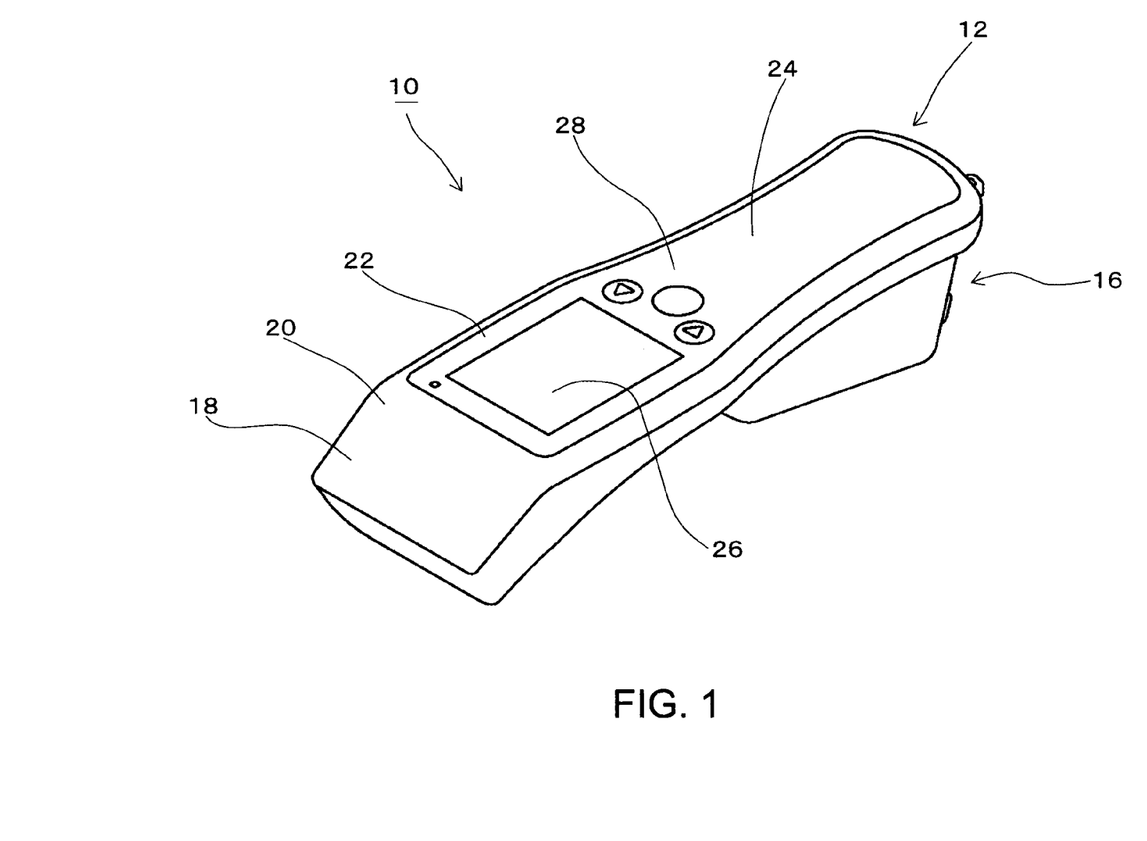
FIG. 1 shows a perspective view of a survey meter as a preferred embodiment of the radiation measurement device according to the present invention.

FIG. 1 shows a preferred embodiment of the radiation measurement device according to the present invention, and FIG. 1 shows a perspective view of a survey meter. This survey meter is a radiation meter for measuring environmental radiation or radiation from radioactive materials. Radiation to be measured is γ-ray.

The survey meter 10 is roughly composed of a body 12 and a battery box 16. The body 12 extends along the longitudinal direction as a whole, and has a flat-plate form. More specifically, the body 12 has a tip portion 18, a middle portion 22, and a grip portion 24. These portions are aligned from the frond side to the rear side along the longitudinal direction. There is a bending portion 20 between the tip portion 18 and the middle portion 22. The body 12 bends at the bending portion 20, and the portion on the front side of the bending portion 20 is the tip portion 18. The tip portion 18 has a radiation detector therein. The middle portion 22 has a display 26 on its upper surface. The display 26 is a liquid crystal display, for example. It displays a dose rate, integral dose, etc. An operating portion 28 is provided between the middle portion 22 and the grip portion 24. In the present embodiment, the operating portion 28 is composed of, for example, three buttons. The grip portion 24 has a form having a neck shape when seen from above; that is, the front side and the rear side of the grip portion are slightly enlarged, and the middle portion therebetween is slightly narrowed.

The battery box 16 is provided on the lower side of the grip portion 24 so as to have a downward protruding form. In the present embodiment, the battery box 16 houses four primary batteries. Each primary battery has a cylindrical form. Naturally, various primary batteries can be used as primary batteries. The survey meter 10 according to the present embodiment can also be equipped with flat-plate shaped secondary batteries therein, and in that case, the battery box 16 is removed. This will be described below by reference to FIG. 9.

Figure 2:
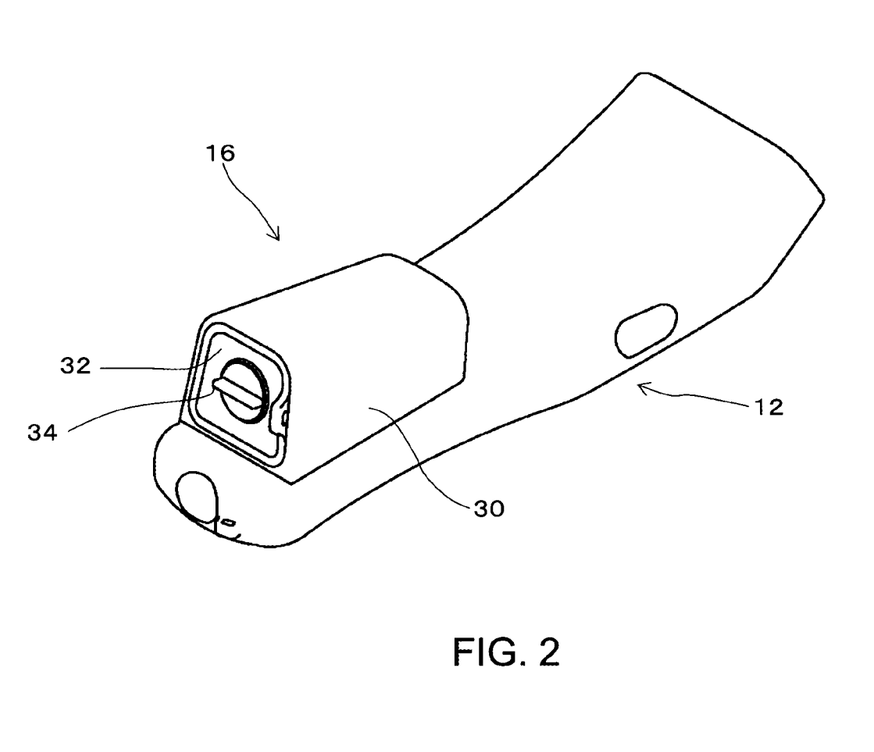
FIG. 2 shows a diagram of the survey meter in FIG. 1 seen from diagonally downward.

FIG. 2 shows the survey meter seen from diagonally downward. As described above, the survey meter is composed of the body 12 and the battery box 16, and the battery box 16 protrudes from the lower side of the grip portion 24. In the present embodiment, the battery box 16 has a hollow housing 30 and a lid 32 that is mounted on an opening of the housing 30. The lid 32 can be removed by rotating operation of a handle 34. In the present embodiment, when the lid 32 is removed, the four primary batteries are inserted into the housing 30. After that, the lid 32 is attached to the opening of the housing 30. A non-metallic seal is provided between the opening and the lid 32 to obtain a good sealing characteristic therebetween.

Figure 3:
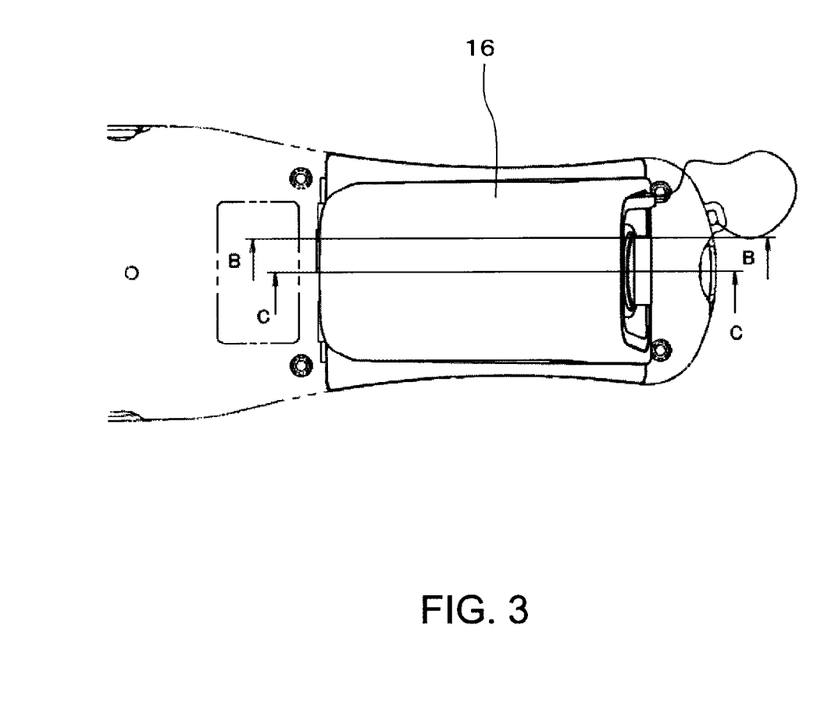
FIG. 3 shows a bottom view of the battery box.
Figure 4:
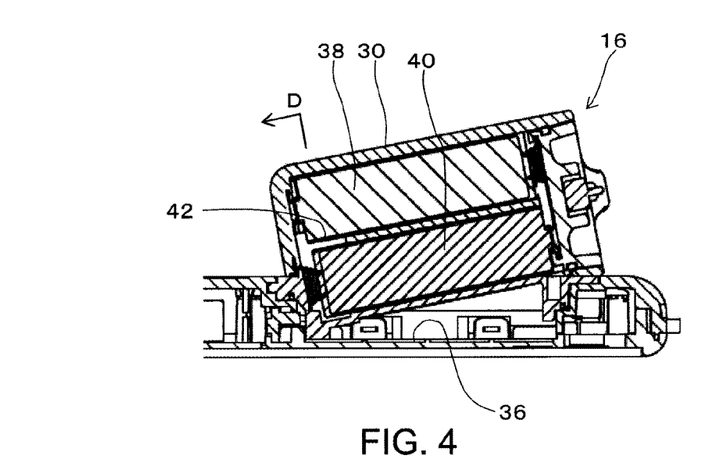
FIG. 4 shows a sectional view taken along B-B in FIG. 3.
Figure 5:
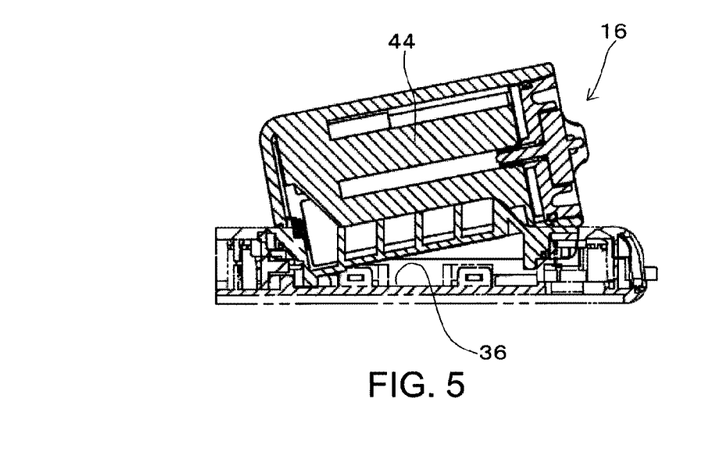
FIG. 5 shows a sectional view taken along C-C in FIG. 3.

FIG. 3 shows the lower surface of the battery box 16. FIG. 4 shows a sectional view taken along B-B, and FIG. 5 shows a sectional view taken along C-C.

In FIG. 4, the battery box 16 has the hollow housing 30. The inside of the housing 30 is a space for housing the four batteries, and, among them, two batteries 38 and 40 are shown in FIG. 4. A housing space 36 is formed in the grip portion of the body of the survey meter. The housing space 36 is a space for housing the plate-shaped second batteries. When the battery box 16 is attached to the body, the opening of the housing space 36 is covered with the housing 30. When the four batteries are inserted into the housing 30, among them, part of two batteries 40 on the body side is inserted into the housing space 36. In the present embodiment, in the battery box 16, the four batteries are arranged in a posture inclined to the body. With such a structure, each battery can easily be inserted into the battery box 16. In addition, as described below, the front surface and the lower surface of the battery box 16 naturally become inclined surfaces.

Although the size of the housing space 36 in the longitudinal direction is smaller than the size of each battery in the longitudinal direction, and the batteries cannot be arranged in the housing space 36 in a horizontal posture, with the above structure, it is possible to suppress the amount of protrusion of the battery box 16 by housing the part of a plurality of batteries in the housing space 36. In FIG. 4, an inclined partition 42 is provided between battery 38 and the battery 40. In FIG. 5, a partition 44 is provided between the two batteries on the right side and the two batteries on the left side.

Figure 6:
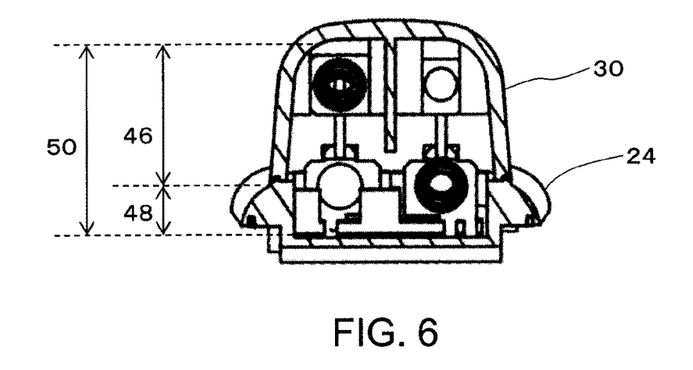
FIG. 6 shows a sectional view of a section indicated by D in FIG. 4.

FIG. 6 shows a section seen from a position D shown in FIG. 4. In FIG. 6, reference number 50 indicates a space for housing the four primary batteries, and the space 50 is roughly composed of an inter-housing space 46 and an inter-body space 48. The inter-body space 48 corresponds to the above-described housing space. It is formed in the grip portion 24. On the inside surface of the front wall of the housing 30, there are arranged terminal members to be connected to the four batteries.

Figure 7:
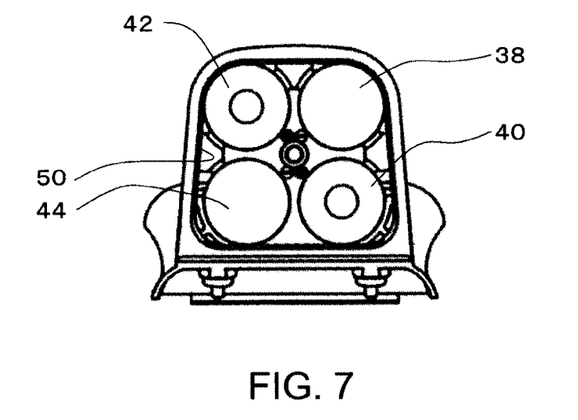
FIG. 7 shows the battery box with the lid removed.

FIG. 7 shows the battery box with the lid removed. The four batteries 38, 40, 42, and 44 are housed in the space 50 in the housing.

Figure 8:
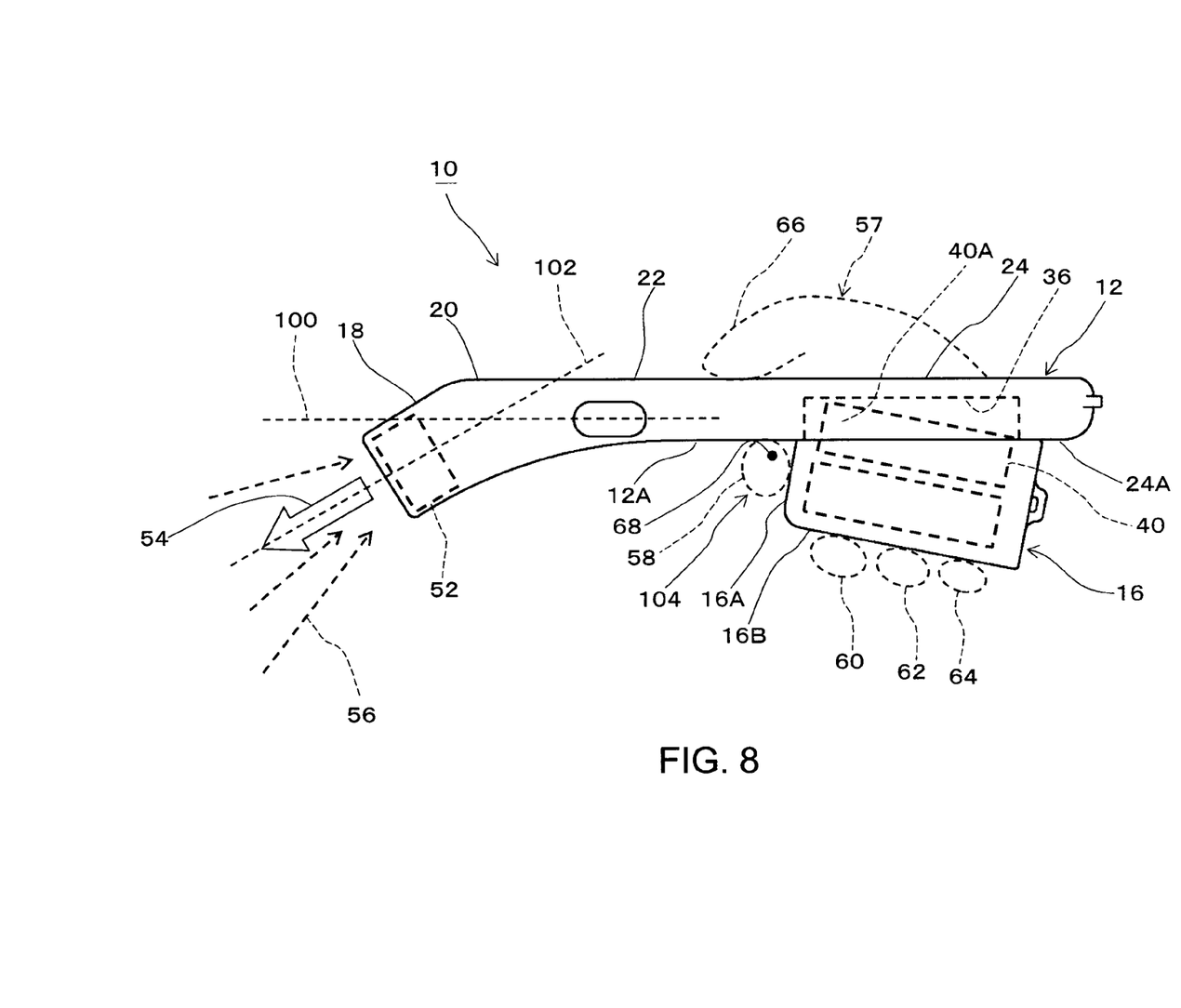
FIG. 8 shows a diagram illustrating effects, etc. of a stepped structure.

FIG. 8 shows a side view of the survey meter 10. The survey meter 10 has the body 12 and the battery box 16, and the body 12 has the tip portion 18, the middle portion 22, and the grip portion 24. The bending portion 20 is disposed between the tip portion 18 and the middle portion 22. This bending portion 20 allows the tip portion 18 to be directed diagonally downward. Reference number 100 indicates the axis line of the body 12, and the axis line is parallel to the longitudinal direction. An axis line 102 indicates the center line of the tip potion 18, and a main sensitivity direction 54 is defined as a direction to which the axis line 102 is directed. A detector 52 is provided in the tip portion 18, and this detector 52 detects γ-rays 56 that come flying from the outside. The detector 52 is a semiconductor detector, for example.

The middle portion 22 and the grip portion 24 in the body 12 have a generally flat-plate form when seen from the lateral direction. The upper surface of the body 12 is a plane surface, and the lower surface 12A is also a substantially plane surface. The battery box 16 is provided so as to protrude downward from the lower surface 12A. As described above, the battery box houses the four batteries therein. The housing of the battery box 16 covers the housing space 36 formed in the body 12. Among the four batteries housed in the battery box 16, a part 40A of the two batteries 40 on the side near the body 12 enters the housing space 36.

The battery box 16 has an inclined lower surface 16B and an inclined front surface 16A. The lower surface 16B is an inclined surface lowered from the front side to the rear side. The angle θ formed between the lower surface 12A and the front surface 16A is less than 90 degrees, and is between 75 to 85 degrees, for example.

A stepped structure 104 is formed over the lower surface 12A and the front surface 16A. The stepped structure 104 enables, for example, the user's index finger 58 to be placed on the front side of the battery box 16. Reference number 68 indicates the center of gravity of the survey meter 10 to which the battery box 16 is attached. In the embodiment shown in FIG. 8, the center of gravity 68 is near the stepped structure 104, and is located slightly lower than the lower surface 12A, and when, for example, the index finger 58 is placed on the stepped structure 104, the survey meter 10 is stabilized on the index finger 58 like a balancing toy.

FIG. 8 shows the survey meter 10 held in a hand 57 in the horizontal state. For example, as described above, the survey meter 10 is held in the hand 57 such that while the index finger 58 of the hand 57 is placed on the stepped structure 104, a middle finger 60, a third finger 62, and a little finger 64 come around on the lower surface 16B. In that case, it is possible to operate buttons constituting the operating portion by a thumb 66, if necessary. Even if the thumb 66 is away from the body 12, the index finger 58 is placed on the stepped structure 104, and therefore, the problem that the survey meter 10 slips off forward from the hand 57 does not arise. Further, because when the survey meter 10 is seen from the side, a holding portion composed of the grip potion 24 and the battery box 16 has a tapered shape or a wedge shape; that is, the holding portion has a form which fits the hand easily, it is possible to hold the survey meter 10 in the hand 57 smoothly. The survey meter 10 may also be held in the hand 57 by placing the four fingers including the index finger 58 on the lower surface 16.

It is also possible to adopt, as the lower surface of the battery box 16, a surface which is parallel to the lower surface 12A of the body 12. In that case, a plurality of batteries are arranged in a horizontal posture. Meanwhile, as in the present embodiment, by adopting the structure in which the front surface 16A is an inclined surface and the lower surface 16B is an inclined surface, it is possible to hold the survey meter 10 more smoothly. Two fingers can be placed on the stepped structure 104. Alternatively, the survey meter may be held so as to wrap the battery box 16 by all the fingers. It is possible to select various ways to hold the survey meter 10 depending on the situation. If the survey meter 10 is inclined forward to measure radiation, by placing at least one finger on the stepped structure 104 as described above, it is easily possible to prevent the survey meter 10 from slipping off forward from the hand 57. Because, in that case, there is also no need for gripping it strongly, the load of holding can be alleviated. Further, because, in such a case, the thumb 66 can be away from the upper surface of the body 12, the advantage of good operability can also be obtained.

Figure 9:
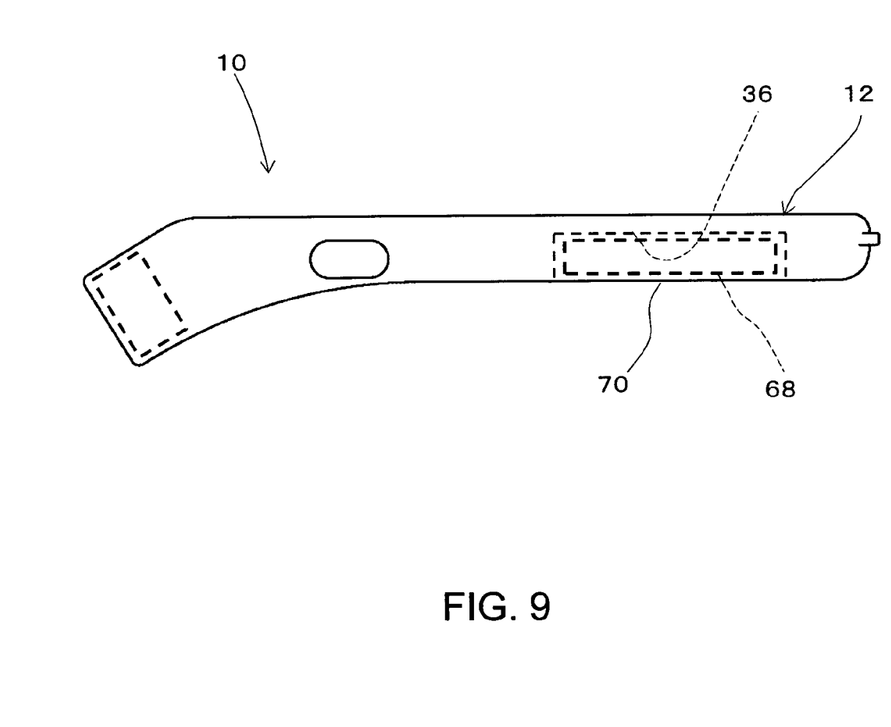
FIG. 9 shows the survey meter with the battery box removed.

FIG. 9 shows the survey meter 10 from which the battery box is removed. A secondary battery 68 is placed in the housing space 36. This secondary battery 68 differs from the primary battery and is rechargeable. Naturally, it is possible to house a rechargeable battery in the battery box. After the plate-shaped secondary battery 68 is set in the housing space 36, the opening of the housing space 36 is closed with a cover 70. As such, for the survey meter 10 according to the present embodiment, it is possible to select either driving by the secondary battery or driving by the primary battery. Further, the survey meter 10 may be structured such that a power cable can be connected. When the battery box is removed, the body 12 has the substantially flat-plate form, and, in this case, the neck shape of the grip portion 24 functions to enable the body 12 to be held in the hand firmly.

The invention claimed is:

1. A portable radiation measurement device, comprising:
a body that has a tip portion for detecting radiation and a grip portion;
a battery box that has a form protruding downward on a lower side of the grip portion and houses one or more batteries, wherein a lower surface of the body and a front surface of the battery box form a corner structure on the lower side of the body;
wherein the one or more batteries are housed in the battery box so as to be in a posture inclined to the body; and
wherein an angle between the lower surface of the body and the front surface of the battery box is less than 90 degrees.

2. The radiation measurement device according to claim 1, wherein a lower surface of the battery box is inclined to the lower surface of the body.

3. The radiation measurement device according to claim 1, wherein the grip portion has a flat-plate form.

4. The radiation measurement device according to claim 1, wherein the battery box has
a housing that houses the one or more batteries, and
a lid that covers an opening formed in a back surface of the housing.

5. The radiation measurement device according to claim 1, wherein:
   the body has the tip portion, a middle portion provided on the rear side of the tip portion, and the grip portion provided on the rear side of the middle portion;
   the body extends in the longitudinal direction; and
   the center of gravity of the radiation measurement device is proximate the step in the longitudinal direction.

* * * * *